United States Patent

Huber

[11] 4,206,765
[45] Jun. 10, 1980

[54] CUFF MECHANISM

[75] Inventor: Thomas G. Huber, St. Petersburg, Fla.

[73] Assignee: Vita-Stat Neducak Services, Inc., St. Petersburg, Fla.

[21] Appl. No.: 825,675

[22] Filed: Aug. 18, 1977

[51] Int. Cl.² .............................................. A61B 5/02
[52] U.S. Cl. ...................................... 128/677; 128/686
[58] Field of Search ...................... 128/2.05 A, 2.05 C, 128/2.05 G, 2.05 M, 2.05 Q, 2.05 P, 2.05 V, 325–327, 75, 84 R, 84 C, 677, 686; 192/55–56

[56] References Cited

U.S. PATENT DOCUMENTS

| | | | |
|---|---|---|---|
| 3,095,873 | 7/1963 | Edmunds, Jr. | 128/2.05 A |
| 3,527,207 | 9/1970 | Gottfried | 128/325 X |
| 3,908,923 | 9/1975 | Salgo | 242/67.3 R X |
| 3,935,984 | 2/1976 | Lichowsky et al. | 128/2.05 C |
| 4,109,646 | 8/1978 | Keller | 128/2.05 C |

FOREIGN PATENT DOCUMENTS 638905  6/1950  United Kingdom ............. 128/2.05 Q Primary Examiner—Robert W. Michell
Assistant Examiner—Francis J. Jaworski
Attorney, Agent, or Firm—Arthur G. Yeager

[57] ABSTRACT

A cuff mechanism, for use in an automatic blood pressure measuring system requiring no user adjustments to such mechanism, includes an elongated flexible cuff band with a resilient spring associated therewith of a predetermined width defining an enlarged opening for receiving a user's arm. A reversible motor intermittently drives a drum through a slip clutch adjusted to provide a snug, but not occluding, fit of the band about the various sized arms when the drum winds up the band into its contracted state. The spring is generally mounted throughout the width of the band and extends substantially throughout the length thereof which defines the opening in its contracted state. The band is attached to the drum substantially throughout the width thereof so that the drum will exert a uniform force to circumferentially contract the band snugly about the arm and to maintain same in a steady condition. Locking means having a manual override automatically locks the drum in its wound-up condition to prevent the band from inadvertent loosening. A flexible and expandable fluid chamber, having a sensor associated therewith, is located adjacent the band and extending generally the width thereof, such chamber being sufficiently elongated to contact and generally surround the arm with the sensor being adjacent the artery. Selective pressure means automatically supply fluid to the chamber to expand same and occlude the flow of blood through the arm after which the blood pressure is taken by the system.

40 Claims, 16 Drawing Figures

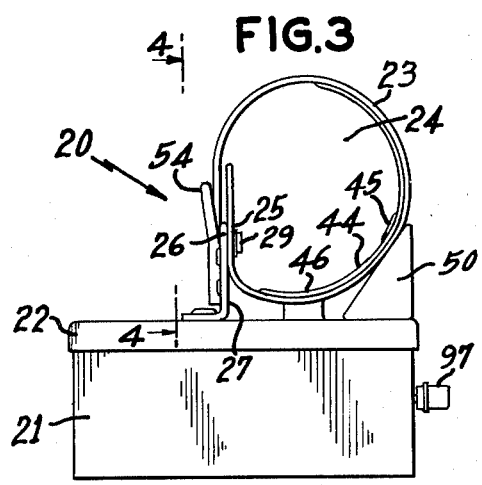
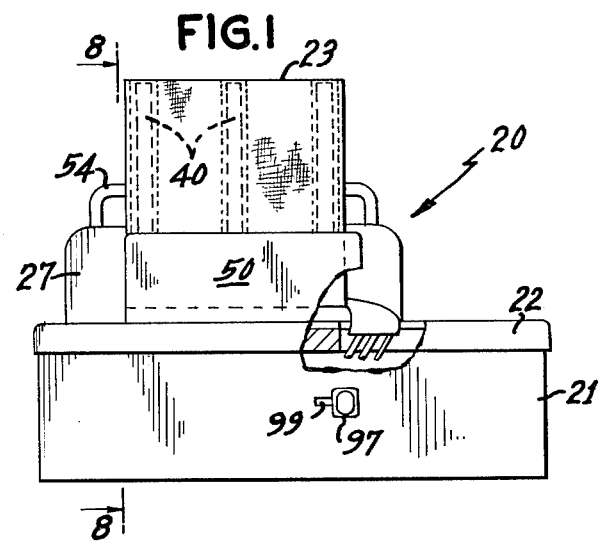
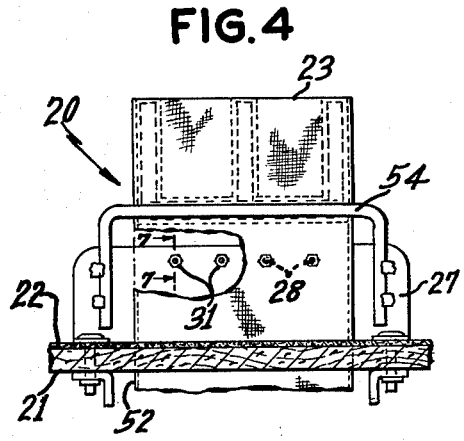
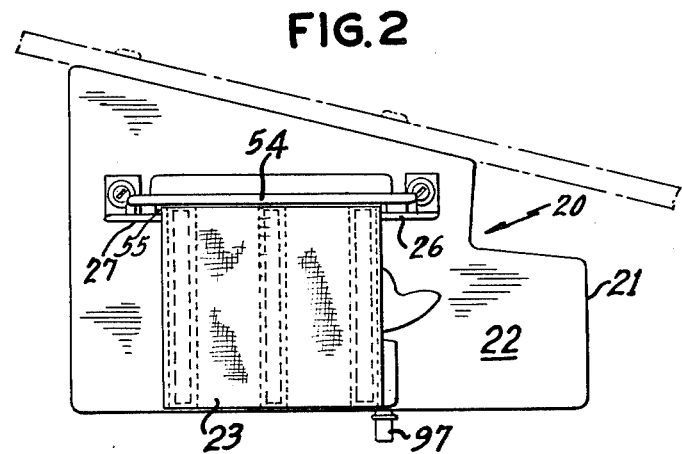
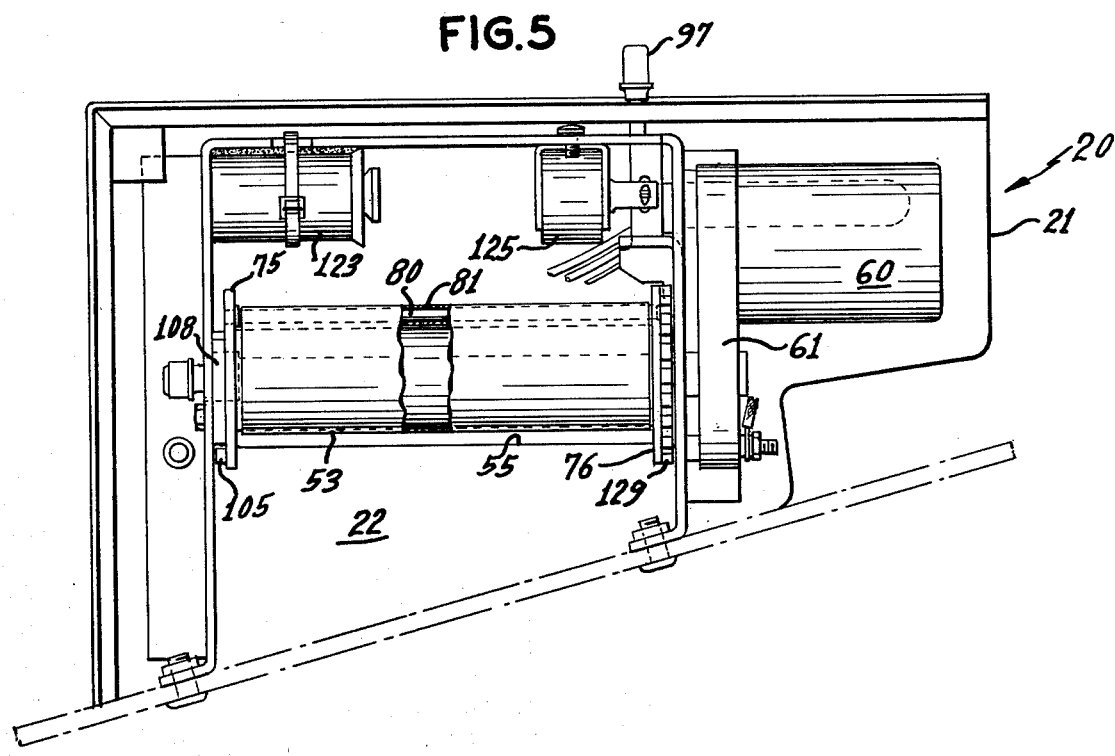

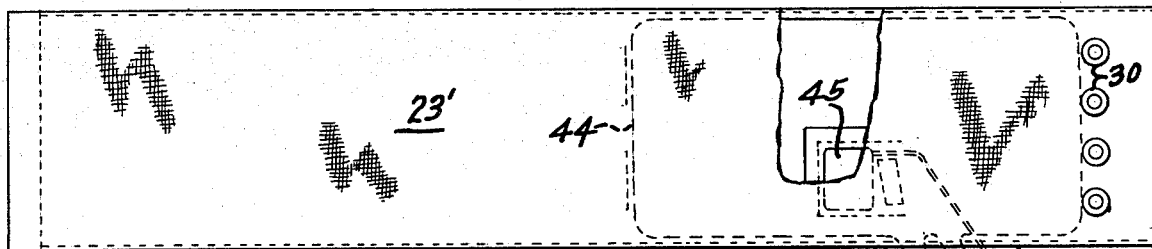
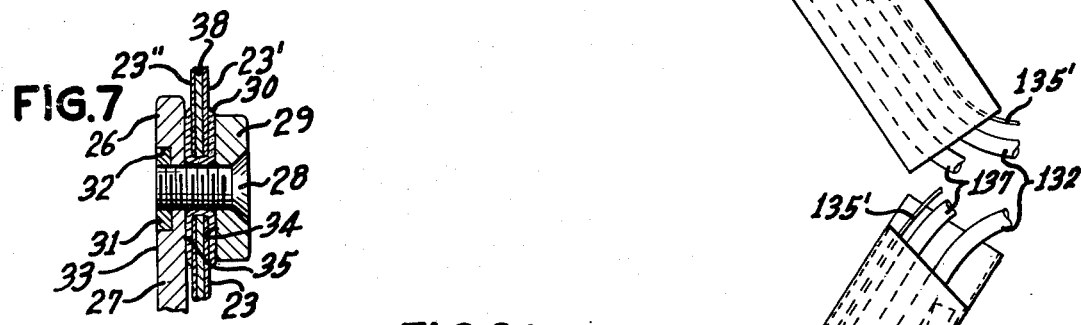
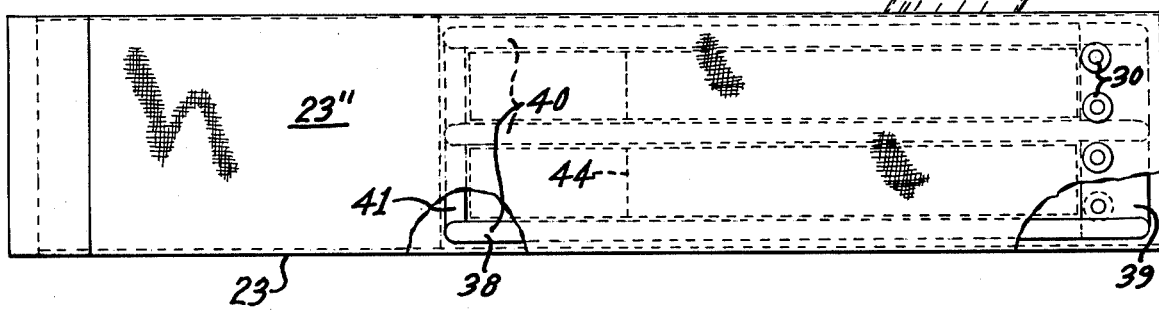
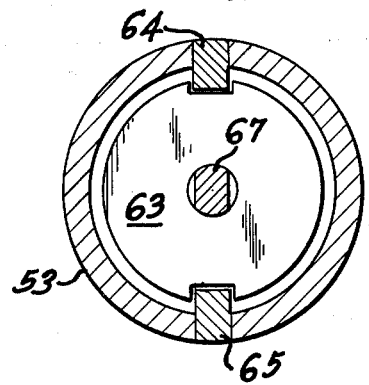
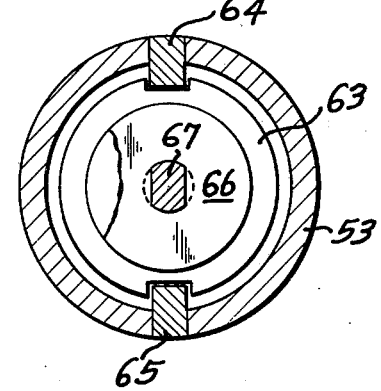

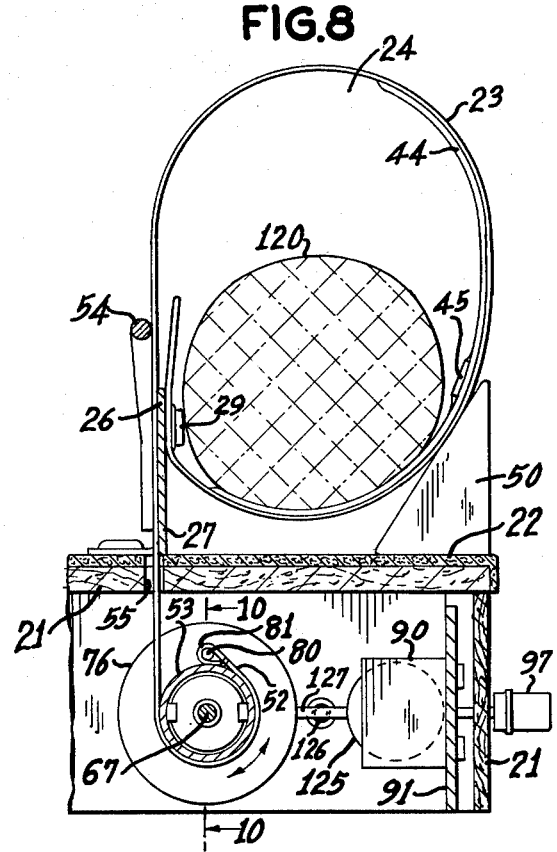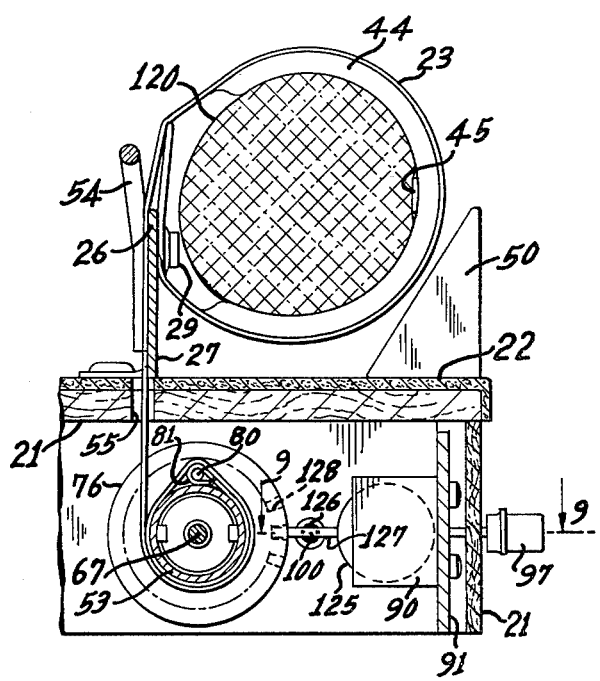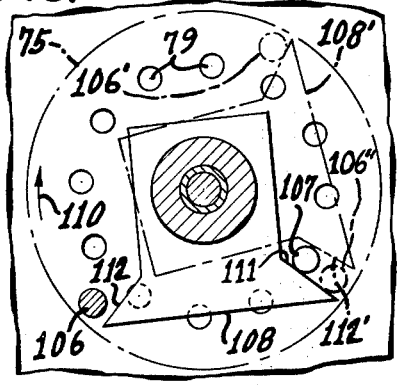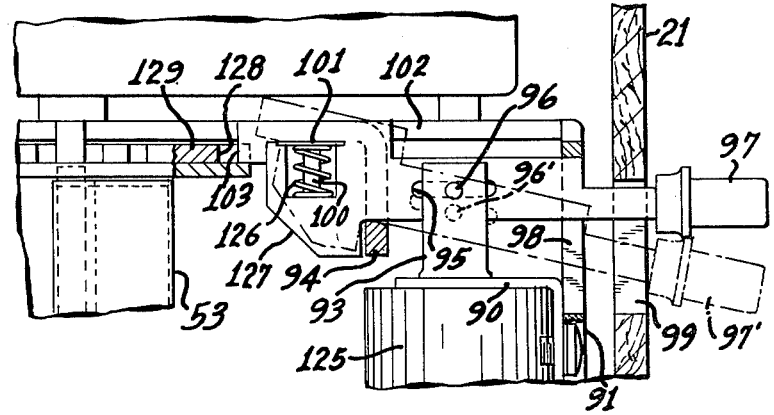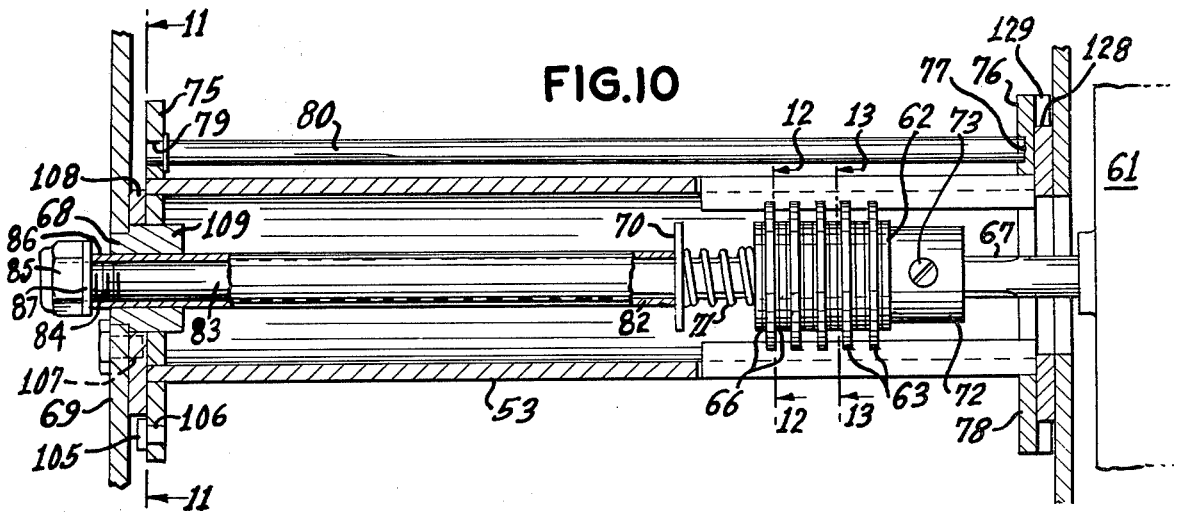

CUFF MECHANISM

BACKGROUND OF THE INVENTION

1. Field of the Invention

This invention relates to cuff mechanisms and more particularly to automatic cuff mechanisms for use in, for example, coin-operated blood pressure measuring systems.

2. Description of the Prior Art

There have been many systems and devices for measuring blood pressure known in the prior art namely U.S. Pat. Nos. 1,946,985—Parker; 2,020,469—Laufman et al; 2,053,383—Telson et al; 2,074,520—Snyder; 2,149,690—Snyder; 2,352,875—Williams et al; 2,375,059—Williams et al; 2,714,379—Raines; 2,865,365—Newland et al; 3,086,513—Newland et al; 3,095,873—Edmunds; 3,101,082—Steen et al; 3,212,499—Koreski; 3,621,631—Pisacano; 3,651,798—Egli et al; 3,757,772—Goldblat et al; 3,841,314—Page; 3,903,872—Link; 3,905,353—Lichowsky; 3,905,354—Lichowsky; 3,906,939—Aronson; 3,908,460—Lichowsky; 3,935,984—Lichowsky; 3,940,742—Hudspeth et al; 3,978,848—Yen et al; 4,008,617—Yen et al; 4,009,709—Link et al; 4,011,860—Lee; and French Patent Nos. 805,599—Emile; and 962,646—Jean-Lugien. The patent to Edmunds—3,095,873 discloses an electrically driven cuff mechanism, one of which has a quick disconnect coupling for adjusting the cuff to match the girth of the arm before further tightening to cause occlusion; the other mechanism having greater similarity to this invention. The patent to Lichowsky 3,935,984 discloses an automatic cuff mechanism in which a flexible band is cable actuated to adjust the cuff to match the girth of the arm before occlusion thereof by a fluid chamber. Various problems are inherent in the above prior art namely, in the Edmunds arrangement some user or another person is required to adjust the cuff and/or is not comfortable and/or provides inaccurate measurements and in the Lichowsky arrangement pinching of the arm as well as other inherent malfunctions are likely to occur. This invention is directed to an improved automatic cuff mechanism which substantially alleviates the problems and deficiencies of the prior art, as will be apparent to those skilled in the art upon consideration of the following specification and drawings.

SUMMARY OF THE INVENTION

In accord with this invention the improved cuff mechanism for use in a blood pressure measuring system includes an elongated flexible cuff band of a predetermined width defining an opening for receiving, for example, an arm of a user in which blood circulation is to be temporarily occluded. The mechanism also includes a contracting means having a relaxed state and a contracted state, such means being attached to the band substantially throughout the width thereof for exerting a force thereon to circumferentially contract the band snugly about the user's arm. Power means intermittingly drives the contracting means through a slippage means connected between the contracting means and the power means to provide relative motion therebetween to attain snug wrapping of the band about various sized arms of different users while preventing occlusion of the blood circulating therethrough. A flexible fluid chamber is located adjacent and inwardly of the band in a position to contact the user's arm for causing the flow of blood therethrough to be occluded; and selective pressure means supply fluid to the chamber to expand same and occlude the flow of blood through the user's arm in contact with the chamber.

Other aspects of the cuff mechanism relate to the provision of means for returning the band to its uncontracted open state after the contracting means returns to its relaxed state. Locking means are provided for selectively locking the contracting means in its contracted state, such locking means including a manual override means for user unlocking of the contracting means to permit release of the band about the user's arm. The power means preferably includes a reversible motor for moving the contracting means between its states in both directions. The contracting means includes a cylinder attached to one end of the band, and the reversible motor drivingly connected to the slippage means in the form of a slip clutch adjusted to provide the appropriate snug fit to the user's arm, such slip clutch in turn driving the cylinder which wraps the band therearound during wind-up or contraction thereof.

A general object of this invention is to provide an improved automatic cuff mechanism for blood pressure measuring systems.

A particular object is the provision of a cuff mechanism which automatically adjusts to the girth of the arm of the user.

Another particular object is to provide a cuff mechanism which is comfortable to various users during tightening of the cuff prior to and during occlusion.

A further particular object is the provision of a cuff mechanism which requires no user adjustment and/or manipulations.

A specific object is to improve the efficiency, quality and reliability of determining the blood pressure of the user in an automatic system. Another specific object is to provide an automatic cuff mechanism that is safe to use and which holds the arm firmly throughout a predetermined width to minimize occurrence of false readings therefrom.

A further specific object is the provision of an improved cuff mechanism which is relatively inexpensive in construction and maintenance and efficient and reliable in operation thereof.

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a right side elevational view of a cuff mechanism in accord with this invention for use primarily in an automatic blood pressure measuring system;

FIG. 2 is a top elevational view thereof;

FIG. 3 is a front elevational view thereof;

FIG. 4 is a partial cross-sectional view taken along line 4—4 of FIG. 3;

FIG. 5 is an enlarged bottom view thereof with the bottom cover removed for clarity of illustration;

FIG. 6 is a flattened view of the inside of the cuff;

FIG. 6A is a flattened view of the outside of the cuff;

FIG. 7 is an enlarged cross-sectional view taken along line 7—7 of FIG. 4;

FIG. 8 is an enlarged cross-sectional view taken along line 8—8 of FIG. 1;

FIG. 8A is a view similar to FIG. 8 but showing the cuff in a tightened condition about the arm of a user;

FIG. 9 is an enlarged cross-sectional view taken along line 9—9 of FIG. 8A;

FIG. 10 is an enlarged cross-sectional view taken along line 10—10 of FIG. 8;

FIG. 11 is a cross-sectional view taken along line 11—11 of FIG. 10;

FIG. 12 is a cross-sectional view taken along line 12—12 of FIG. 10;

FIG. 13 is a cross-sectional view taken along line 13—13 of FIG. 10; and

DETAILED DESCRIPTION OF THE PREFERRED EMBODIMENT

Figure 14:
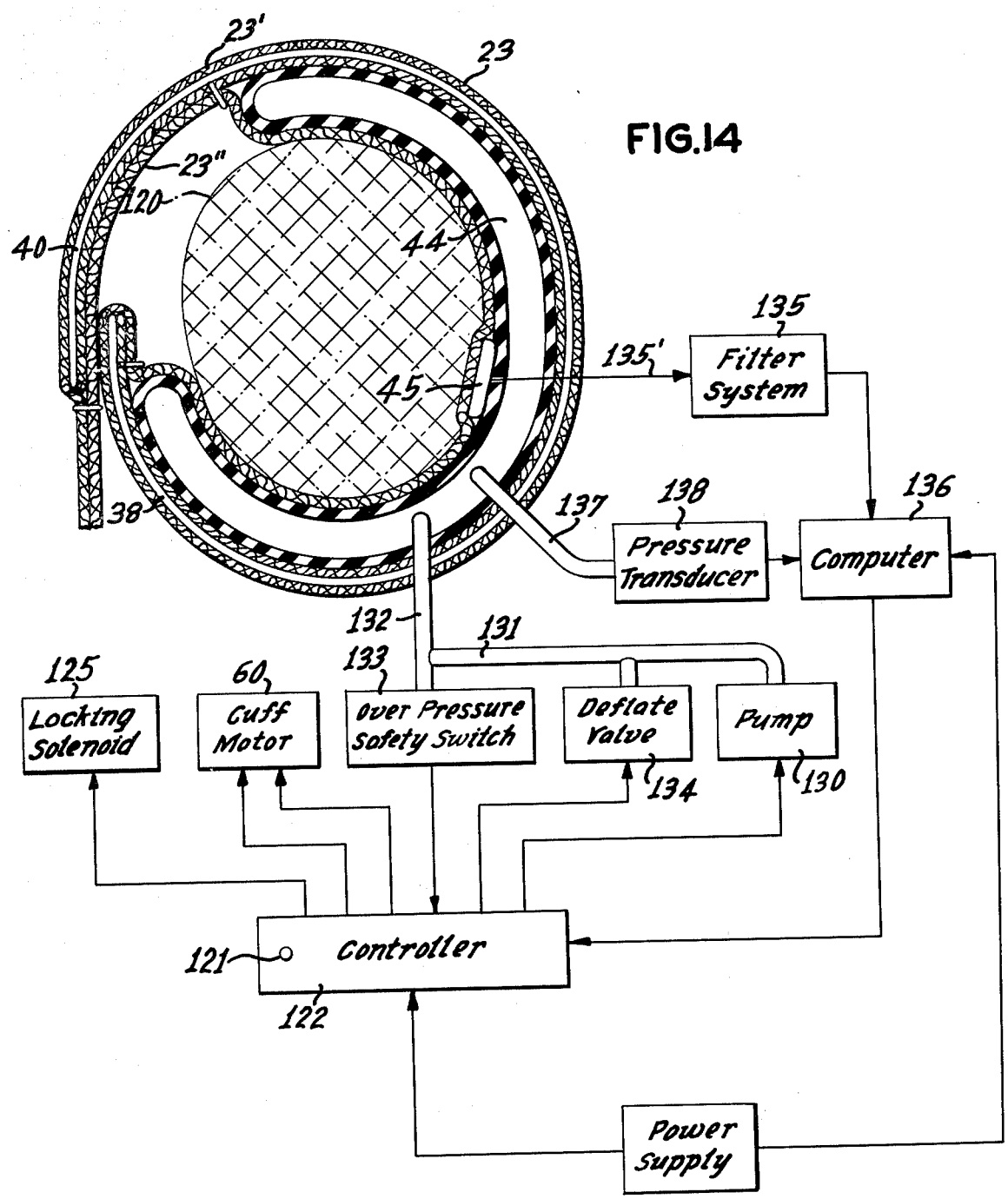
FIG. 14 is an enlarged diagrammatic view of the cuff and a block diagram of the system for automatically determining a user's blood pressure.

Referring now more particularly to FIGS. 1–5, the cuff mechanism is generally indicated by numeral 20 and comprises a housing 21 having a top plate 22 supporting the cuff means in the form of an elongated band 23 defining an opening 24 for the reception of a portion of a user's body, for example, an arm in which blood circulation is to be occluded, i.e., during the blood pressure measurement of both systolic and diastolic pressures in a manner hereinafter more fully described in connection with FIG. 14.

As seen in FIGS. 3, 4 and 7, the band 23 is affixed at one end portion 25 to the upper end portion 26 of an L-shaped plate support 27 by suitable fasteners in the form of spaced flat headed bolts 28 and washers, including washer 29, engaging spaced grommets, including grommet 30, attached to band 23. Nuts 31 are threaded onto bolts 28 and lie flush within recesses, including recess 32, within the remote surface 33 of support 27. Thus, the belt 23 and the attached grommets 30 are sandwiched between the facing surfaces 34 and 35 of respective washers 29 and support 27, as clearly illustrated in FIG. 7. Preferably, the band 23 includes internal and external fabric coverings 23' and 23" not only to protect the other components within the band 23 but to insure non-abrasive and comfortable gripping of the arm during operation thereof.

The belt 23, as seen in FIG. 6A, includes resilient means in the form of a flat spring means 38 having a base 39, through which the grommets 30 extend, and three spaced and elongated fingers or stays 40 extend from base 39 to a remote cross arm 41, spaced along belt 23 remote from base 39. The length of the stays 40 is sufficient to approximately surround the girth of a normal sized arm when the belt 23 is in its contracted state therearound. Located on the other side of the stays 40 is a flexible and elongated fluid chamber 44 extending from adjacent base 39 of spring means 38 and terminating short of cross arm 41. The length of the chamber 44 is sufficient to approximately surround about three-quarters of the girth of a normal sized arm so that when the chamber 44 is pressurized, after the belt 23 has been contracted to snugly fit the arm of a user, the expanse of the chamber will forcibly squeeze the arm to occlude the main artery of the arm. An accoustical cavity or sensor 45 is attached on the exterior wall 46 of chamber 44, sensor 45 being located generally to overlie the main artery of the user's arm in a manner well known in the art.

Returning now to FIGS. 1–5, an arm rest 50 of a generally triangular cross-section is spaced laterally of upright support 27, and provides a supporting surface for the band 23 in its open condition. As hereinbefore described band end portion 25 is secured to support 27 while the other end portion 52 is attached to a contracting means in the form of a cylinder or drum 53 located within housing 21 generally below the opening 24 defined by band 23. Upon rotation of drum 53, band 23 wraps therearound by exerting a pulling force thereon substantially downwardly with the band passing outwardly of upright support 27 and guided by upright member 54, which is spaced closely adjacent to and substantially parallel to support 27, and thence through slot 55 in the top plate 22, as clearly depicted in FIGS. 8 and 9.

Power means in the form of an electrically reversible motor 60 drives through a reducing gear train 61 and a slippage means in the form of a slip clutch 62 within the drum 53, as shown in FIG. 10. The slip clutch 62 includes a plurality of large disks 63 suitably keyed by opposing keys 64 and 65 to drum 53 so that the disks 63 rotate therewith. Small disks 66 rotate with shaft 67 which is driven through gear train 61 by motor 60. Shaft 67 extends through hollow drum 53 and is suitably journaled by bearing 68 mounted in support 69 spaced remotely from gear train 61. Shaft 67 includes a moveable stop 70 on which one end of a compression spring 71 abuts while the other end thereof is juxtaposed with the closest one of the small disks 66. A shaft coupling in the form of a stationary stop 72 is slidingly disposed on splined shaft 67 and is affixed thereto in a predetermined position by set screw 73 such that the band 23 will be generally contracted with a sufficient degree of snugness about the arm of the user regardless of the girth of such arm. This feature is in direct contrast to the mechanism of 3,935,984 in which the motor automatically stops due to the design thereof to exert only a given torque.

The means for adjusting the slip clutch 62 includes moveable stop 70 in contact with compression spring 71, elongated sleeve 82 slidingly telescoped about shaft 83 which has a threaded end portion 84 extending outwardly of support 69. An adjusting nut 85 is threaded onto end portion 84 and forcibly engages, via washer 87, the adjacent end 86 of sleeve 82 whereby tightening of the nut 85 will move the sleeve 82 and washer 70 toward spring 71 and increase compressive force of spring 71 resulting in the slip clutch 62 only slipping at a higher resistance, i.e., the motor 60 will apply a greater wrapping force to the band 23 around the arm of the user. In order to prevent any undue tightening, nut 85 is adjusted so that the belt is snugly, but comfortably wrapped about the arm of the user before occlusion thereof by the fluid chamber 44, as hereinbefore previously described.

A pair of spaced plates 75 and 76 are connected to drum 53 a predetermined distance slightly larger than the width of band 23. Spaced depressions 77 are provided in the surface 78 of plate 76 facing plate 75 and plate 75 has aligned openings 79 therethrough whereby pin 80 may be adjusted to lengthen or shorten band 23 which has a looped end 81 through which pin 80 extends to affix the band 23 to drum 53 for wind-up around pin 80 and drum 53, as clearly depicted in FIGS. 8 and 8A.

Locking solenoid 125 is supported by bracket 90 on frame 91 mounted within housing 21. The solenoid core 93 is shown in FIG. 9 in its deactivated normal state with lever 127 engaged within a depression 128 of gear wheel 129. Lever 127 is rockingly supported by arm 94 mounted to frame 91 and includes an elongated slot 95 disposed generally aligned with and connected to core 93 by pin 96. When the solenoid 125 is activated, the core 93 retracts downwardly, as shown in FIG. 9, to the broken line position 96' of pin 96 thereby forcing lever downwardly at the end 97 as shown by broken lines 97', extending outwardly through slot 98 of frame 91 and slot 99 of housing 21 for manual release or override of the solenoid 125. Thereafter when the solenoid 125 is deactivated, the compressed spring 126, which is mounted to lever 127 by being positioned around rod 100, engages a sliding washer 101 spanning slot 102 in frame 91 for forcibly returning lever 127 into one of the gear depressions 128 aligned with lever end 102, as will be apparent to persons skilled in the art. If a depression does not precisely align with the lever end 103, a ratchet action takes place so that the next adjacent depression is engaged.

Considering FIGS. 10 and 11, disk 75 is mounted to cylinder 53 for rotation therewith and a lug 105 having a shaft 106 is fixed to disk 75 and extends toward frame support 69. A lug 107 is shifted to support 69 and forms a stop for engagement with a cam 108 located between support 69 and disk 75 and functionally mounted on member 109. When the cam 108 is in its full line position as seen in FIG. 11, and the drum 53 begins to rotate in the direction of arrow 110, cam surface 112 is not in engagement with lug 105 (and its shaft 106). Lug 105 and shaft 106 move with drum 53 and disk 75 until cam surface 111 is engaged by lug 105 attached at the broken line position to shaft 106", i.e., cam 108 is thus picked up by drum 53. When the cam 108 rotates to its broken line position 108', cam surface 112' engages stop lug 107 affixed to support 69 whereupon further rotation of drum 53 and disk 75 to tighten band 23 will be prohibited, thus causing slip clutch 62 to slip, and the cam will remain in its broken line position 108'. Upon reverse rotation of the drum 53 and disk 75, in which lug 105 with its associated shaft 106 should be in broken line position 106', lug 105 will rotate counterclockwise with its shaft to its broken line position 106" which will engage cam surface 112' and rotate the cam, which stops when surface 111 engages stop 107, back to its original full line position 108 regardless of the girth of the arm 120 which was removed from the band 23, thus assuring the same amount of band defining the opening 24 each time the mechanism is reused. As may be seen, the cam 108 is rotatable in a range of 360° or less while the drum is rotatable less than 360° independent of the arm. The net result is that the drum 53 may rotate more than 360° but less than 720° thus providing a large amount of band to define a large opening 24 while assuring a snug fit during contraction thereof.

The operation of the cuff mechanism will be more clearly understood by reference to FIGS. 5, 8, 8A, 9, 10 and 14. The user's arm 120 is inserted in the opening 24 in the band's relaxed or open state and the start button 121 is depressed (or in coin operated starter is used) to activate the controller 122 which energizes capacitor 123 in the forward position to turn cuff motor 60 on and simultaneously to energize solenoid 125 to release the locking lever 127 whereby the drum 53 is rotated to contract band 23 snugly around the arm 120. When the band 23 contacts the arm 120, the pre-adjusted slip clutch 62, begins slipping as the preset degree of snugness thereby obtaining a uniformly snug and wrapped cuff about the arm regardless of the size of the arm inserted therein, and, of course, to prevent overtightness and/or occlusion of the blood passing through the artery of the arm.

After the motor 60 has been powered for about five (5) seconds, the power thereto is decoupled from the capacitor 123 by controller 122 and the motor 120 stops simultaneously the locking solenoid is de-energized to permit compression spring 126 to move locking lever 127 into engagement with one of the plurality of depressions or notches 128 of drum plate in the form of a gear 129, which is rotatably connected to drum 53, thereby inhibiting reverse rotation or slippage of drum 53 during subsequent inflation of chamber 44. Controller 122 thereupon activates the fluid pump 130 to pressurize chamber 44 through tubes 131 and 132 to cause occlusion of the artery of the arm. An over pressure safety switch 133 is provided to prevent over pressurization of the chamber 44 by pump 130. If over pressure is detected by switch 133, a signal is provided to controller 122 which may open deflate valve 134 and/or deactivate pump 130. The fluid in chamber 44 is then released by action of the controller opening deflate valve 134 (normally open prior activation of start button 121 but closed prior to pump 130 being activated) until the time as appropriate pulses are detected by sensor 45 which are supplied by line 135' to filter system 135 for producing appropriately filtered signals which are delivered to computer 136. Other signals through pressure tube 137 communicating between pressure transducer 138 and chamber 44 which signals are supplied to the computer 136 and subsequently the pre-programmed computer 136 determines and displays the measured systolic and diastolic pressures of the user for a predetermined length of time or until start button 121 is again actuated. When both pressures have been determined, the remaining fluid exits from the chamber 44 via tubes 132 and 131 and out through valve 134. Controller 122 actuates the reverse position of capacitor 123 which reverses motor 60 to move the drum 53 clockwise from its wound up positions as seen in FIG. 8, whereby the band 23 is backed off drum 53 to its initial start position, as shown in FIG. 8A. The leaf spring stays 40, being temporarily bent into the wound up position about the arm of the user, resiliently return the band 23 to its completely open state, as shown in FIG. 8, when the band 23 has been backed off by motor 60. Also, the same amount of band 23 defining the opening 24 is assured by the action of the cam 108, as hereinabove substantially described in connection with FIGS. 10 and 11.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A cuff mechanism for use in a blood pressure measuring system comprising:
   a. an elongated flexible cuff band of a predetermined width defining an opening for receiving a portion of a user's body in which blood circulation is to be temporarily occluded;
   b. mechanical contracting means having a relaxed state and a contracted state and being attached to said band substantially throughout the width thereof for exerting a force thereon to circumferentially contract said band snugly about the portion of the user's body;

c. power drive means for intermittingly driving said mechanical contracting means;

d. automatic and adjustable slip clutch means connected between said mechanical contracting means and said power drive means to provide relative motion therebetween after obtaining snug wrapping of said band about various sized body portions of different users and slipping thereafter to prevent occlusion of the blood circulating therethrough, said slip clutch means including a slip clutch between said power drive means and said mechanical contracting means, and an adjustable means engaged with said slip clutch for selectively adjusting said slip clutch to slip upon said band reaching a predetermined snug fit;

e. a flexible fluid chamber located adjacent said band and in position to contact the portion of a user's body for causing the flow of blood therethrough to be occluded; and f. selective pressure means for supplying fluid to said chamber to expand same and occlude the flow of blood through the portions of the user's body in contact with said chamber.

2. The cuff mechanism as defined in accord with claim 1 further comprising:

g. means for returning said band to its uncontracted open state after said mechanical contracting means returns to its relaxed state.

3. The cuff mechanism as defined in claim 2 wherein said means for returning said band includes a spring.

4. The cuff mechanism as defined in claim 3 wherein said spring is mounted to said band substantially throughout the length thereof defining said opening in its contracted state.

5. The cuff mechanism as defined in claim 4 wherein said spring is mounted to said band generally throughout the width thereof.

6. The cuff mechanism as defined in claim 3 wherein said spring is mounted to said band generally throughout the width thereof.

7. The cuff mechanism as defined in claim 2 wherein said mechanical contracting means includes a drum attached to one end of said band, said means for returning said band including a lost motion device between said drum and a fixed housing support adjacent thereto for returning said band to its fully uncontracted state regardless of the girth of the portion of the user's body which was previously contracted by said band.

8. The cuff mechanism as defined in claim 1 further comprising:

g. locking means for selectively locking said mechanical contracting means in its contracted state.

9. The cuff mechanism as defined in claim 8 wherein said locking means includes a manual override means for unlocking said mechanical contracting means by the user to permit release of the user body portion by said band.

10. The cuff mechanism as defined in claim 1 wherein said power drive means is includes a reversible motor for moving said mechanical contracting means between its said states.

11. The cuff mechanism as defined in claim 10 wherein said mechanical contracting means includes a drum attached to one end of said band, said motor being drivingly connected to said slip clutch means which in turn drives said drum.

12. The cuff mechanism as defined in claim 1 further comprising:

g. a base support, said cuff band having its inner end affixed to and disposed above said support and said contracting means being disposed therebelow, said support having a slot therethrough outwardly of said band inner end for the passage of the outer end of said band therethrough, said outer end a said band being attached to said contracting means for reducing the cross-sectional dimension of said opening; and h. means for returning said band to its fully open state.

13. A cuff mechanism including a housing for use in a blood pressure measuring system comprising:

a. an elongated flexible cuff band of a predetermined width defining an opening for receiving an arm of a user's body in which blood circulation is to be temporarily occluded; said band having one end attached to said housing;

b. drum means mounted to said housing and being attached to the other end of said band substantially throughout the width thereof for exerting a force thereon to circumferentially contract said band snugly about the arm inserted into said opening;

c. power drive means within said housing for intermittingly driving said drum means;

d. automatic and adjustable slip clutch means connected between said drum means and said power drive means to provide relative motion therebetween after obtaining snug wrapping of said band about various sized arms of different users while slipping thereafter to prevent occlusion of the blood circulating therethrough, said slip clutch means including a slip clutch between said power drive means and said mechanical contracting means, and an adjustable means engaged with said slip clutch for selectively adjusting said slip clutch to slip upon said band reaching a predetermined snug fit;

e. a flexible fluid chamber located adjacent said band and in position to contact the arm for causing the flow of blood therethrough to be occluded upon proper pressurization thereof; and f. selective pressure means for supplying fluid to said chamber to expand same and occlude the flow of blood through the arm in contact with said chamber.

14. The cuff mechanism as defined in accord with claim 13 further comprising:

g. means for returning said band to its fully open state after said drum means returns to its original state with said band unwrapped therefrom.

15. The cuff mechanism as defined in claim 13 wherein said cuff band defining said opening is above said housing, said drum means being located within said housing, said housing including an elongated slot of a predetermined width for accomodating same therethrough.

16. The cuff mechanism as defined in claim 15 wherein said opening is generally above said drum means, with the portion of said band extending through said slot being substantially vertical.

17. The cuff mechanism as defined in claim 16 further comprising guide means mounted to said housing and extending parallel to and spaced adjacent to said one band end for guiding said band through said slot.

18. The cuff mechanism as defined in claim 13 wherein said drum means includes a cylinder on which said band is wrapped, a disk having spaced depressions thereon being rotatable with said cylinder, and selective locking means engageable with selected said depressions for locking said cylinder in selected positions.

19. The cuff mechanism as defined in claim 18 wherein said selective locking means includes an electrically operated lever having one end engaged with selected said depressions.

20. The cuff mechanism as defined in claim 19 wherein said lever extends outwardly of said housing for engagement by the user to manually override the locking of said lever in selected said depressions.

21. The cuff mechanism as defined in claim 19 wherein said locking means further includes a spring for biasing said lever toward said depressions.

22. The cuff mechanism as defined in claim 18 wherein said selective locking means includes a lever having one end engageable with selected said depressions, and, a solenoid being connected to said lever spaced from said end for unlocking said lever end from selected said depressions.

23. The cuff mechanism as defined in claim 22 wherein said locking means further includes a spring biasing said lever toward said depressions.

24. The cuff mechanism as defined in claim 23 wherein said lever has another end graspable by the user to manually override the locking action thereof.

25. The cuff mechanism as defined in claim 13 further comprising:
   g. locking means for selectively locking said drum means when said band has been wound therearound to cause a snug fit about the arm.

26. The cuff mechanism as defined in claim 25 wherein said locking means includes a manual override means for unlocking said drum means by the user to permit release of the arm by said band.

27. The cuff mechanism as defined in claim 26 wherein said drum means includes a cylinder attached to said slip clutch means which in turn drives said cylinder.

28. The cuff mechanism as defined in claim 13 further comprising a lost motion means between said cylinder and said housing to return said band to its original open condition regardless of the girth of the arm previously inserted into said opening and contracted by said band.

29. The cuff mechanism as defined in accord with claim 28 further comprising:
   g. means for returning said band to its fully open state after said cylinder returns to its original state with said band unwrapped therefrom.

30. The cuff mechanism as defined in claim 28 wherein said lost motion means comprises a cam mounted for rotation about the same axis as said drum, a pair of lugs one of which being stationary and the other being moveable and mounted to said drum for rotation therewith, said drum being rotatable in one direction less than 360° for engagement with said cam, said cam contacting said stationary lug in a range of rotation of 360° or less after cam engagement by said moveable cam whereby rotation of said drum ceases and said slip clutch begins slipping.

31. A cuff mechanism for use in a blood pressure measuring system comprising:

a. an elongated flexible cuff band of a predetermined width defining an opening for receiving a portion of a user's body in which blood circulation is to be temporarily occluded;

b. mechanical contracting means having a relaxed state and a contracted state and being attached to said band substantially throughout the width thereof for exerting a force thereon to circumferentially contract said band snugly about the portion of the user's body, said mechanical contracting means including a drum attached to one end of said band;

c. power drive means for intermittingly driving said mechanical contracting means;

d. automatic slip clutch means connected between said mechanical contracting means and said power drive means to provide relative motion therebetween after obtaining snug wrapping of said band about various sized body portions of different users and slipping thereafter to prevent occlusion of the blood circulating therethrough;

e. a flexible fluid chamber located adjacent said band and in position to contact the portion of a user's body for causing the flow of blood therethrough to be occluded;

f. selective pressure means for supplying fluid to said chamber to expand same and occlude the flow of blood through the portion of the user's body in contact with said chamber; and g. means for returning said band to its uncontracted open state after said mechanical contracting means returns to its relaxed state, said means for returning said band including a lost motion device between said drum and a fixed housing support adjacent thereto for returning said band to its fully uncontracted state regardless of the girth of the portion of the user's body which was previously contracted by said band.

32. The cuff mechanism as defined in claim 11 wherein said slip clutch means comprises a slip clutch adjusted to provide the appropriate snug fit of said band to the user's body portion.

33. The cuff mechanism as defined in claim 32 wherein said slippage means further comprises means for adjusting said slip clutch.

34. A cuff mechanism including a housing for use in a blood pressure measuring system comprising:

a. an elongated flexible cuff band of a predetermined width defining an opening for receiving an arm of a user's body in which blood circulation is to be temporarily occluded; said band having one end attached to said housing;

b. drum means mounted to said housing and being attached to the other end of said band substantially throughout the width thereof for exerting a force thereon to circumferentially contract said band snugly about the arm inserted into said opening, said mechanical contracting means including a drum attached to one end of said band;

c. power drive means within said housing for intermittingly driving said drum means;

d. automatic slip clutch means connected between said drum means and said power drive means to provide relative motion therebetween after obtaining snug wrapping of said band about various sized arms of different users while slipping thereafter to prevent occlusion of the blood circulating therethrough;

e. a flexible fluid chamber located adjacent said band and in position to contact the arm for causing the flow of blood therethrough to be occluded upon proper pressurization thereof;

f. selective pressure means for supplying fluid to said chamber to expand same and occlude the flow of blood through the arm in contact with said chamber; and g. means for returning said band to its uncontracted open state after said mechanical contracting means returns to its relaxed state, said means for returning said band including a lost motion device between said drum and a fixed housing support adjacent thereto for returning said band to its fully uncontracted state regardless of the girth of the portion of the user's body which was previously contracted by said band.

35. The cuff mechanism as defined in claim 34 wherein said means for returning said band includes a spring.

36. The cuff mechanism as defined in claim 35 wherein said spring is mounted to said band substantially throughout the length thereof defining said opening.

37. The cuff mechanism as defined in claim 36 wherein said spring is mounted to said band generally throughout the width thereof.

38. The cuff mechanism as defined in claim 35 wherein said spring is mounted to said band generally throughout the width thereof.

39. The cuff mechanism as defined in claim 34 wherein said power drive means includes a reversible motor for moving said drum in directions to wind-up and unwind said band about the arm.

40. The cuff mechanism as defined in claim 39 wherein said slip clutch means comprises a slip clutch, and means for adjusting said slip clutch to provide the appropriate snug fit of said band about the arm.

* * * * *